United States Patent

Street

Patent Number: 5,514,682
Date of Patent: May 7, 1996

[54] FUSED IMIDAZOLE AND TRIAZOLE DERIVATIVES AS 5-HT1 RECEPTOR AGONISTS

[75] Inventor: Leslie J. Street, Harlow, United Kingdom

[73] Assignee: Merck Sharp & Dohme Limited, Hoddesdon, England

[21] Appl. No.: 335,800

[22] PCT Filed: May 6, 1993

[86] PCT No.: PCT/GB93/00936

§ 371 Date: Nov. 14, 1994

§ 102(e) Date: Nov. 14, 1994

[87] PCT Pub. No.: WO93/23396

PCT Pub. Date: Nov. 25, 1993

[30] Foreign Application Priority Data

May 15, 1992 [GB] United Kingdom ............ 92 10 400.9

[51] Int. Cl.⁶ .................. A61K 31/52; A61K 31/435; C07D 473/00; C07D 471/04
[52] U.S. Cl. .................. 514/266; 514/303; 514/394; 544/277; 546/118; 548/207; 548/241; 548/305.1
[58] Field of Search .................. 546/118; 544/277; 548/305.1, 207, 241; 514/303, 266, 394

[56] References Cited

U.S. PATENT DOCUMENTS 5,298,520  3/1994  Baker et al. .................. 514/383

FOREIGN PATENT DOCUMENTS

0200322A1  11/1986  European Pat. Off. .
0313397A1  4/1989  European Pat. Off. .
92/06973  4/1992  WIPO .

*Primary Examiner*—Bernard Dentz
*Attorney, Agent, or Firm*—Robert J. North; Melvin Winokur

[57] ABSTRACT

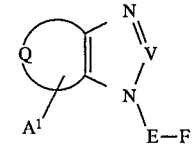

(I)

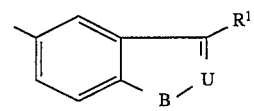

(a)

Compounds of formula (I) wherein F represents a Group of the formula (a) ; E represents a bond or a straight or branched alkylene chain containing from 1 to 4 carbon atoms; and the rest of the variables are defined in the specification are selective agonists of $5HT_1$-like receptors and are therefore useful in the treatment of clinical conditions, in particular migraine and associated disorders, for which a selective agonist of these receptors is indicated.

9 Claims, No Drawings

FUSED IMIDAZOLE AND TRIAZOLE DERIVATIVES AS 5-HT1 RECEPTOR AGONISTS

The present invention relates to a class of fused imidazole and triazole derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

The present invention provides a compound of formula I, or a salt or prodrug thereof:

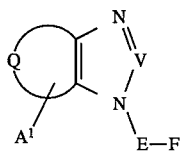

(I)

wherein

Q represents the residue of a six-membered aromatic or heteroaromatic nucleus containing zero, one or two nitrogen atoms;

A$^1$ represents hydrogen, hydrocarbon, a heterocyclic group, halogen, cyano, trifluoromethyl, —OR$^x$, —SR$^x$, —NR$^x$R$^y$, —NR$^x$COR$^y$, —NR$^x$CO$_2$R$^y$, —NR$^x$SO$_2$R$^y$, or —NR$^z$CTNR$^x$R$^y$;

V represents nitrogen or C—A$^2$;

E represents a bond or a straight or branched alkylene chain containing from 1 to 4 carbon atoms;

F represents a group of formula

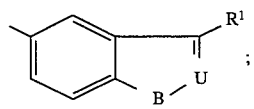

U represents nitrogen or C—R$^2$;

B represents oxygen, sulphur or N—R$^3$;

R$^1$ represents —CH$_2$.CHR$^4$.NR$^6$R$^7$ or a group of formula (i), (ii), (iii) or (iv):

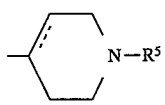

(i)

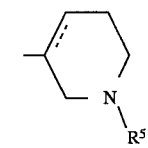

(ii)

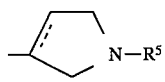

(iii)

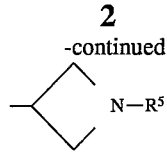

(iv)

in which the broken line represents an optional chemical bond;

A$^2$, R$^2$, R$^3$, R$^4$, R$^5$, R$^6$ and R$^7$ independently represent hydrogen or C$_{1-6}$ alkyl;

R$^x$ and R$^y$ independently represent hydrogen, hydrocarbon or a heterocyclic group, or R$^x$ and R$^y$ together represent a C$_{2-6}$ alkylene group;

R$^z$ represents hydrogen, hydrocarbon or a heterocyclic group;

T represents oxygen, sulphur or a group of formula =N.G; and

G represents hydrocarbon, a heterocyclic group or an electron-withdrawing group.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$) alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

A particular aryl group is phenyl.

Particular aryl($C_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$) alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $NR^vR^w$, $-NR^vCOR^w$, $-NR^vCO_2R^w$, $-NR^vSO_2R^w$, $-CH_2NR^vSO_2R^w$, $-NH-CONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, $-COR^x$, $-CO_2R^x$ or $-SO_2R^x$, in which $R^x$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

The six-membered aromatic or heteroaromatic nucleus of which Q is the residue in the compounds of formula I as defined above is a benzene, pyridine, pyridazine, pyrimidine or pyrazine nucleus. Thus, the compounds of formula I may suitably be represented by structure IA:

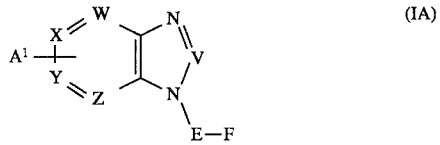

in which zero, one or two of W, X, Y and Z represent nitrogen and the remainder represent carbon; and $A^1$, V, E and F are as defined above.

In a suitable embodiment, W represents nitrogen, X and Z each represents carbon and Y represents nitrogen or carbon.

In an alternative embodiment, Z represents nitrogen, W and Y each represents carbon and X represents nitrogen or carbon.

Preferably, V represents CH.

The alkylene chain E may be, for example, methylene, ethylene, 1-methylethylene, propylene or 2-methylpropylene. Alternatively, the group E may represent a single bond such that the group F in formula I is attached directly to the five-membered heteroaromatic ring.

The group F is suitably an indole, benzofuran or benzthiophene moiety of formula FA, or an indazole moiety of formula FB:

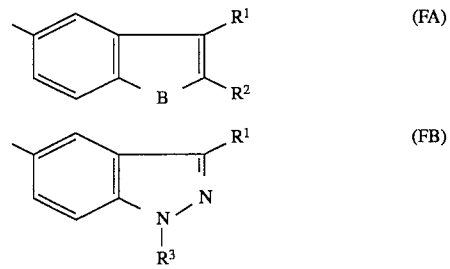

wherein B, , $R^1$ $R^2$ and $R^3$ are as defined above. Preferably, the group F represents an indole moiety of structure FC:

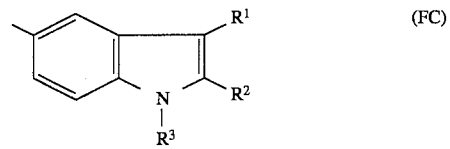

wherein $R^1$, $R^2$ and $R^3$ are as defined above, in particular wherein $R^2$ and $R^3$ are both hydrogen.

Suitable values for the group $A^1$ include $C_{1-6}$ alkyl, $C_{3-7}$ cycloalkyl, aryl, aryl($C_{1-6}$) alkyl, $C_{3-7}$ heterocycloalkyl, heteroaryl, heteroaryl($C_{1-6}$)alkyl, $C_{1-6}$ alkoxy or $C_{1-6}$ alkylthio, any of which groups may be optionally substituted; and hydrogen, halogen, cyano, trifluoromethyl or $-NR^xR^y$, in which $R^x$ and $R^y$ are as defined above. Examples of optional substituents on the group $A^1$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$) alkylamino, $C_{1-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^1$ include hydrogen, methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl, methoxypyridylmethyl, amino, methylamino, benzylamino, dimethylamino, t-butoxycarbonylaminoethylamino and methylsulphonylaminoethylamino.

Preferably, $A^1$ is hydrogen.

Representative values of $R^1$ include aminoethyl, N-methylaminoethyl, N,N-dimethylaminoethyl, 4-piperidyl, 1-methyl-4-piperidyl, 3-pyrrolidinyl, 1-methyl-3-pyrrolidinyl, 3-azetidinyl and 1-methyl-3-azetidinyl.

Preferred values for the groups $R^2$ to $R^7$ are hydrogen and methyl.

A particular sub-class of compounds according to the invention is represented by the compounds of formula IIA, and salts and prodrugs thereof:

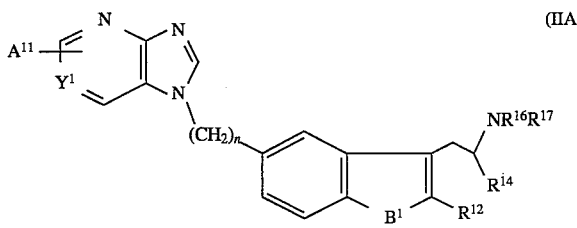

(IIA)

wherein $Y^1$ represents nitrogen or carbon;

n is zero, 1, 2 or 3;

$B^1$ represents oxygen, sulphur or N—$R^{13}$;

$A^{11}$ represents $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, $C_{1-6}$ alkylamino or di($C_{1-6}$) alkylamino, any of which groups may be optionally substituted; or hydrogen, halogen, cyano, trifluoromethyl or amino; and $R^{12}$, $R^{13}$, $R^{14}$, $R^{16}$ and $R^{17}$ independently represent hydrogen or $C_{1-6}$ alkyl.

Examples of optional substituents on the group $A^{11}$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkyl-aminosulphonylmethyl.

Preferably, $A^{11}$ is hydrogen.

Preferably, $R^{12}$, $R^{13}$ and $R^{14}$ each represents hydrogen. Preferred values of $R^{16}$ and $R^{17}$ with respect to formula IIA include hydrogen and methyl.

Another sub-class of compounds according to the invention is represented by the compounds of formula IIB, and salts and prodrugs thereof:

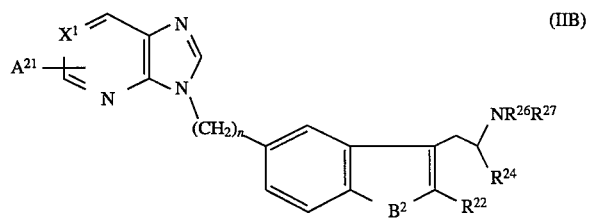

(IIB)

wherein $X^1$ represents nitrogen or carbon;

n is zero, 1, 2 or 3;

$B^2$ represents oxygen, sulphur or N—$R^{23}$;

$A^{21}$ represents $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino; and $R^{22}$, $R^{23}$, $R^{24}$, $R^{26}$ and $R^{27}$ independently represent hydrogen or $C_{1-6}$ alkyl.

Examples of optional substituents on the group $A^{21}$ correspond to those indicated for the group $A^{11}$ with respect to formula IIA above. Preferably, $A^{21}$ is hydrogen.

Preferably, $R^{22}$, $R^{23}$ and $R^{24}$ each represents hydrogen. Preferred values of $R^{26}$ and $R^{27}$ with respect to formula IIB include hydrogen and methyl.

Specific compounds within the scope of the present invention include:

N,N-dimethyl-2-[5-(4-azabenzimidazol-1-yl)-1H-indol-3yl]ethylamine;

N,N-dimethyl-2-[5-(4,6-diazabenzimidazol-1-yl)-1H-indol-3-yl]ethylamine;

N,N-dimethyl-2-[5-(4,6-diazabenzimidazol-1-ylmethyl)-1H-indol- 3-yl]ethylamine;

N,N-dimethyl-2-[5-(5,7-diazabenzimidazol-1-ylmethyl)-1H-indol- 3-yl]ethylamine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to this invention wherein the group F is an indole moiety of structure FC as defined above may be prepared by a process which comprises reacting a compound of formula III:

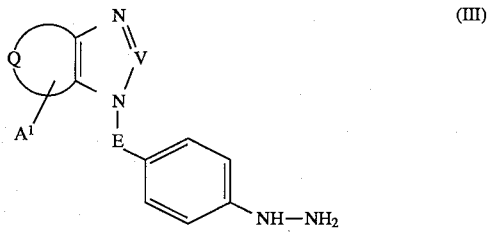

wherein Q, $A^1$, V and E are as defined above; with a compound of formula IV or a carbonyl-protected form thereof:

wherein $R^2$ is as defined above and $R^{11}$ corresponds to the group $R^1$ as defined above or a protected derivative thereof, or represents a group of formula —$CH_2.CHR^4D^1$, in which $R^4$ is as defined above and $D^1$ represents a readily displaceable group; followed, where required, by N-alkylation by standard methods to introduce the moiety $R^3$; and, if necessary, by removal of any protecting groups.

Suitable carbonyl-protected forms of the compounds of formula IV include the dimethyl acetal or ketal derivatives.

The readily displaceable group $D^1$ in the compounds of formula IV suitably represents a halogen atom, preferably chlorine. When the moiety $R^{11}$ in the compounds of formula IV is a group of formula —$CH_2.CHR^4D^1$, the substituent $D^1$ is displaced in situ under the prevailing reaction conditions to afford a final product of formula I wherein $R^1$ represents a group of formula —$CH_2.CHR^4.NH_2$. The terminal amino group can subsequently, if desired, be further elaborated using techniques known from the art to give a compound of formula I wherein $R^1$ represents the required group of formula —$CH_2.CHR^4.NR^6R^7$.

Where $R^1$ in the final product of formula I represents an azetidinyl moiety of formula (iv) as hereinbefore defined, the reagent of formula IV of use in the above reaction, in which $R^{11}$ corresponds to a protected derivative of the group $R^1$, may suitably be represented by structure IVA:

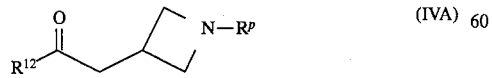

wherein $R^2$ is as defined above and $R^P$ represents an amino-protecting group.

Suitable examples of amino-protecting groups for the substituent $R^P$ include carboxylic acid groups such as chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as benzyl, p-methoxybenzyl, trityl, o-nitrophenylsulphenyl or benzylidene.

Preferred amino-protecting groups include t-butoxycarbonyl, benzyloxycarbonyl and p-methoxybenzyl.

The removal of the protecting group present in the resultant compound may be effected by an appropriate procedure depending upon the nature of the protecting group. Typical procedures include hydrogenation in the presence of a palladium catalyst (e.g. palladium carbon or palladium black) for benzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl and trityl groups; treatment with hydrogen bromide in glacial acetic acid or trifluoroacetic acid for benzyloxycarbonyl, p-bromobenzyloxycarbonyl, p-phenylazobenzyloxycarbonyl and t-butoxycarbonyl groups; treatment with acetic acid and/or a mineral acid such as hydrochloric acid or sulphuric acid for trityl, t-butoxycarbonyl, formyl and benzylidene groups; and treatment with 2,3-dichloro-5,6-dicyano-1,4-benzoquinone for p-methoxybenzyl groups.

The reaction of compounds III and IV may be carried out in a single step (Fischer indole synthesis) or by an initial non-cyclising step at a lower temperature to give a compound of formula V:

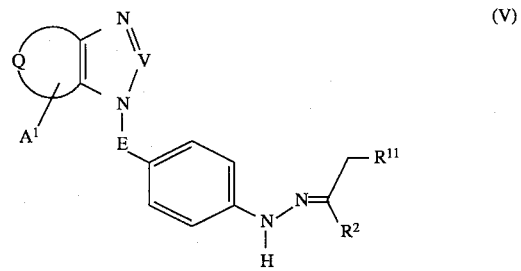

wherein Q, $A^1$, V, E, $R^2$ and $R^{11}$ are as defined above; followed by cyclisation using a suitable reagent, such as a polyphosphate ester.

The hydrazines of formula III may be prepared from the corresponding anilines of formula VI:

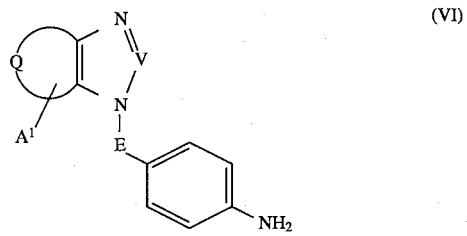

wherein Q, $A^1$, V and E are as defined above; by diazotisation followed by reduction. Diazotisation is typically carried out using sodium nitrite/conc. HCl and the resulting diazo product reduced in situ using, for example, tin(II) chloride/conc. HCl, sodium sulphite/conc. HCl, or sodium sulphite/conc. $H_2SO_4$.

The anilines of formula VI may be prepared by reduction of the corresponding nitro compounds of formula VII:

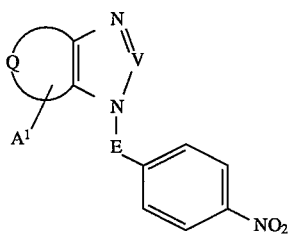
(VII)

wherein Q, $A^1$, V and E are as defined above; typically by transfer hydrogenation using a hydrogenation catalyst such as palladium on charcoal in the presence of a hydrogen donor such as ammonium formate, or alternatively by conventional catalytic hydrogenation or using tin(II) chloride.

The nitro compounds of formula VII may be prepared by a variety of methods which will be readily apparent to those skilled in the art. One such method involves reacting a compound of formula VIII with a compound of formula IX:

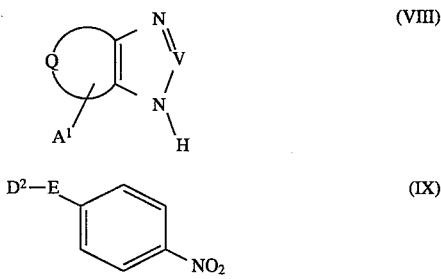
(VIII)

(IX)

wherein Q, $A^1$, V and E are as defined above, and $D^2$ represents a readily displaceable group.

The reaction is conveniently carried out in the presence of sodium hydride using N,N-dimethylformamide as solvent.

The readily displaceable group $D^2$ in the compounds of formula IX is suitably a halogen atom, preferably bromine; except when the moiety $D^2$ is attached directly to the aromatic ring, i.e. when E represents a bond, in which case $D^2$ is preferably fluorine.

It will be appreciated that a mixture of positional isomers is obtainable from the reaction between compounds VIII and IX, since nucleophilic displacement of the group $D^2$ by either of the two nitrogen atoms depicted in the five-membered ring in formula VIII is roughly equally likely in principle. This will be so unless the six-membered ring of which Q is the residue is symmetrical, i.e. unless the pairs of atoms W/Z and X/Y as depicted in structure IA above are identical and $A^1$ is hydrogen. Where a mixture of isomers is indeed obtained from this reaction, separation of the isomers may conveniently be effected by conventional techniques such as column chromatography.

The compounds according to the invention wherein the group F is an indazole moiety of structure FB as defined above may be prepared by a process which comprises the cyclisation of a compound of formula X:

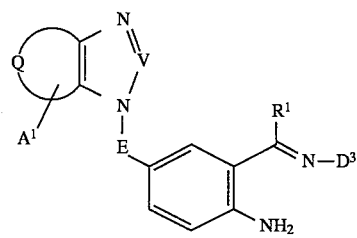
(X)

where Q, $A^1$, V, E and $R^1$ are as defined above; and $D^3$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^3$ in the compounds of formula X suitably represents a $C_{1-4}$ alkanoyloxy group, preferably acetoxy. Where $D^3$ in the desired compound of formula X represents acetoxy, this compound may be conveniently prepared by treating a carbonyl compound of formula XI:

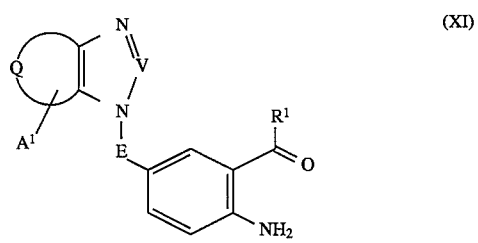
(XI)

wherein Q, $A^1$, V, E and $R^1$ are as defined above; or a protected derivative thereof; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula XI may be conveniently prepared by ozonolysis of an indole derivative of formula XII:

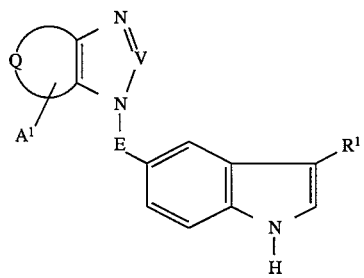
(XII)

wherein Q, $A^1$, V, E and $R^1$ are as defined above; followed by a reductive work-up, advantageously using dimethylsulphide.

The indole derivative of formula XII may be prepared by methods analogous to those described in the accompanying Examples, or by procedures well known from the art.

In a further process, the compounds according to the invention wherein the group F is a benzofuran or benzthiophene moiety may be prepared by a method which comprises cyclising a compound of formula XIII:

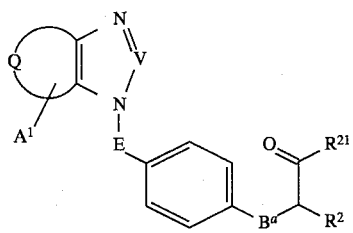

(XIII)

wherein Q, $A^1$, V, E and $R^2$ are as defined above, $B^a$ represents oxygen or sulphur, and $R^{21}$ corresponds to the group $R^1$ as defined above or represents a precursor group thereto as discussed below; followed, where required, by conversion of the group $R^{21}$ into the desired group $R^1$ by conventional means.

The cyclisation is conveniently effected by using polyphosphoric acid or a polyphosphate ester, advantageously at an elevated temperature.

The compounds of formula XIII may be prepared by reacting a compound of formula XIV with a compound of formula XV:

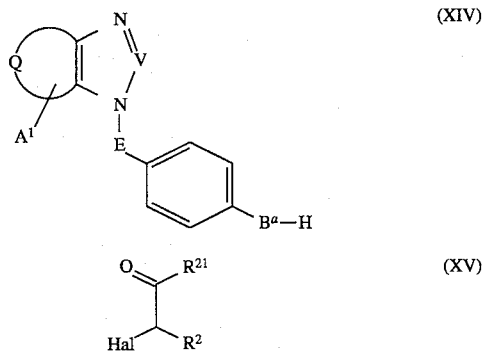

(XIV)

(XV)

wherein Q, $A^1$, V, E, $B^a$, $R^2$ and $R^{21}$ are as defined above, and Hal represents halogen.

The reaction is conveniently effected in the presence of a base such as sodium hydroxide.

The hydroxy and mercapto derivatives of formula XIV may be prepared by a variety of methods which will be readily apparent to those skilled in the art. In one such method, a compound of formula VIII as defined above is reacted with a compound of formula XVI:

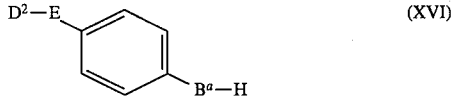

(XVI)

wherein $D^2$, E and $B^a$ are as defined above.

In a still further process, the compounds according to the invention wherein E is other than a chemical bond may be prepared by a process which comprises reacting a compound of formula VIII as defined above with a compound of formula $D^4$—$E^1$—F, wherein F is as defined above, $E^1$ represents a straight or branched alkylene chain containing from 1 to 4 carbon atoms, and $D^4$ represents a group which is capable of being displaced during the course of the reaction.

The displaceable group $D^4$ suitably represents hydroxy, in which case the reaction is advantageously carried out in the presence of triphenylphosphine and diethyl azodicarboxylate, ideally in an organic solvent such as tetrahydrofuran at room temperature.

Alternatively, the group $D^4$ may be a conventional leaving group such as a halogen atom, for example bromine, or a trialkylammonium group, for example trimethylammonium. Where $D^4$ represents bromine, the reaction is conveniently carried out in the presence of a mild base, e.g. potassium carbonate, suitably in an organic solvent such as N,N-dimethylformamide, at a temperature of between 10° C. and 100° C., ideally at room temperature. Where $D^4$ represents trimethylammonium, the reaction is conveniently carried out in the presence of a strong base such as sodium hydride, suitably in an organic solvent such as N,N-dimethylformamide, and ideally at a temperature in the region of 90° C.

As with that between compounds VIII and IX, the reaction between compounds VIII and $D^4$—$E^1$—F, as well as that between compounds VIII and XVI, is capable of giving rise to mixtures of positional isomers which, as before, may conveniently be separated by conventional techniques such as column chromatography.

Where they are not commercially available, the intermediates of formula $D^4$—$E^1$—F may be prepared by procedures analogous to those described in the accompanying Examples, or by methods well known from the art. For example, those compounds wherein $D^4$ is halogen may be prepared from the corresponding compounds of formula $D^4$-$E^1$-F in which $D^4$ is hydroxy using standard halogenation techniques. Alternatively, those compounds wherein $D^4$ is a trialkylammonium group may be prepared from the corresponding compounds of formula $D^4$-$E^1$-F in which $D^4$ represents dialkylamino by quaternisation using a suitable alkyl iodide in conventional manner.

The intermediates of formula IV, VIII, IX, XV and XVI, where they are not commercially available, may be prepared by methods analogous to those described in the accompanying Examples, or by procedures known from the art. In particular, the intermediates of formula VIII may be prepared by procedures analogous to those described in Comprehensive Heterocyclic Chemistry, ed. A. R. Katritzky and C. W. Rees, Pergamon Press, Oxford, 1984, vol. 5.

The preparation of a typical protected azetidinyl intermediate of formula IVA is illustrated by the following reaction scheme:

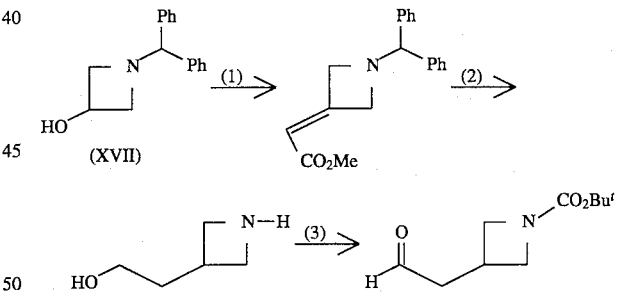

The starting compound XVII is known from J. Chem. Soc., Chem Commun., 1968, 93. Step 1 of the reaction scheme comprises oxidation of the hydroxy group of compound XVII to a carbonyl group using pyridine. $SO_3$ in dimethyl sulphoxide (DMSO) and triethylamine; followed by reaction of the resulting azetidinone derivative with the Horner-Emmons reagent $MeO_2C.CH_2.PO(OEt)_2$ in the presence of sodium hydride, using tetrahydrofuran (THF) as the solvent. In Step 2, the double bond of the azetidine olefin ester is hydrogenated over palladium-charcoal in methanol; the methyl ester group is then reduced to hydroxymethyl by treatment with lithium aluminium hydride in THF; and the diphenylmethyl protecting group is in turn removed by treatment with palladium hydroxide on charcoal, with methanol serving as the solvent. Step 3 involves protection of the azetidine nitrogen as the N-t-butoxycarbonyl (N-BOC) carbamate derivative; and, finally, Swern oxidation of the side chain terminal hydroxy group to an aldehyde moiety by treatment with oxalyl chloride in DMSO/triethylamine.

It will be understood that any compound of formula I initially obtained from any of the above processes may, where appropriate, subsequently be elaborated into a further compound of formula I by techniques known from the art. In particular, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide. Similarly, a compound of formula I wherein $R^1$ represents a group of formula —$CH_2.CHR^4.NH_2$ initially obtained may be converted into a compound of formula I wherein $R^1$ represents a group of formula —$CH_2.CHR^4.NR^6R^7$ in which $R^6$ and $R^7$ independently represent $C_{1-6}$ alkyl, by conventional N-alkylation techniques, e.g. by treatment with the appropriate aldehyde in the presence of a reducing agent such as sodium cyanoborohydride.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Alternatively, certain of the functional groups on the desired products may be carried through the reaction sequence as precursor groups, and then regenerated from these precursor groups at a late stage in the overall synthesis. For example, where $R^1$ in the desired compound of formula I represents a group of formula —$(CH_2)_2NH_2$, this group can be generated from a cyano precursor —$CH_2CN$ by reduction using, for example, borane/tetrahydrofuran. The cyano precursor may in turn be carried through the reaction sequence as a methyl group —$CH_3$, which may conveniently be converted to —$CH_2CN$ by treatment with N-bromosuccinimide and benzoyl peroxide, in the presence of a bright light source, followed by reaction of the resulting bromo intermediate with sodium cyanide in dimethyl sulphoxide.

The following Examples illustrate the preparation of compounds according to the invention.

The ability of test compounds to bind to 5-$HT_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-$HT_{1A}$ and 5-$HT_{1C}$ binding sites respectively. The concentration of the compounds of the accompanying Examples required to displace 50% of the specific binding ($IC_{50}$) is below 1 µM in each case.

The activity of test compounds as agonists of the 5-$HT_1$-like receptor was measured in terms of their ability to mediate contraction of the saphenous vein of New Zealand White rabbits, using the procedure described in *Arch. Pharm.*, 1990, 342, 111. Agonist potencies were calculated as $-\log_{10}EC_{50}$ ($pEC_{50}$) values, from plots of percentage 5-HT (1 µm) response against the concentration of the agonist. The compounds of the accompanying Examples were found to Possess $PEC_{50}$ values in this assay of not less than 5.0 in each case.

EXAMPLE 1

N.N-Dimethyl-2-[5-(4-azabenzimidazol-1-yl)-1H-indol-3-yl) ehylamine, Oxalate, Monohydrate.

1. 4-(4-Azabenzimidazol-1-yl)nitrobenzene

Sodium hydride (2.02 g, 84.0 mmol, 60% dispersion in oil) was added to a solution of 4-azabenzimidazole (10.0 g, 84.0 mmol) in DMF (120 ml). The mixture was stirred at room temperature for 0.25 h before adding 1-fluoro-4-nitrobenzene (11.86 g, 84.0 mmol) and stirring for 2 h. A precipitate formed which was filtered off and washed with $Et_2O$ (100 ml) and acetone (50 ml). The product was dried under vacuum to afford the title-product (10.0 g, 50%); δ (250MHz, $D_6$-DMSO) 7.40–7.48 (1H, m, Ar—H), 8.06 (2H, d, J=9.0Hz, Ar—H), 8.24 (1H, d, J=9.0Hz, Ar—H), 8.46 (2H, d, J=9.0Hz, Ar—H), 8.56 (1H, dd, J =1.0 and 3.5Hz, Ar—H), 9.04 (1H, s, Ar—H).

2. 4-(4-Azabenzimidazol-1-yl )phenylaniline

10% Pd—C (1.0 g) was added to a mixture of the preceding nitrobenzene (10.0 g, 42.0 mmol), 1N HCl (350 ml) and methanol (200 ml) and hydrogenated at 40 psi in a Parr flask for 3 h. The catalyst was removed by filtration through celite and the solvent removed under vacuum. The residue was taken up into $H_2O$ (20 ml), basified ($K_2CO_3$) and extracted with $CH_2Cl_2$ (5 x). The combined extracts were dried ($Na_2.SO_4$) and evaporated and the residue chromatographed on silica gel, eluting with $CH_3Cl_2$/MeOH (95:5) to give the desired aniline (6.45 g, 74%); δ (360MHz, $CD_2OD$) 6.76 (2H, d, J=9.0Hz, Ar—H), 7.18 (2H, d, J=9.0Hz, Ar—H), 7.27 (1H, dd, J=5.0 and 8.0Hz, Ar—H), 7.84 (1H, dd, J=1.0 and 8.0Hz, Ar—H), 8.37 (1H, dd, J=1.5 and 5.0Hz, Ar—H), 8.41 (1H, s, Ar—H).

3. 4-(4-Azabenzimidazol-1-yl )phenylhydrazine

A solution of $NaNO_2$ (2.35 g, 34.0 mmol) in $H_2O$ (30 ml) was added to a stirred solution of the preceding aniline (6.45 g, 31.0 mmol) in conc$^n$.HCl (60 ml), cooled to –15° C. After addition the mixture was stirred for 0.5 h at –15° C. and then filtered through a sinter directly into an addition funnel. The resulting solution was added to a rapidly stirred solution of $SnCl_2.2H_2O$(28.0 g, 0.12 mol) in conc$^n$. HCl (50 ml) at such a rate as to maintain the temperature below –5° C. The mixture was warmed to room temperature, the precipitate filtered off and washed several times with $Et_2O$. In order to remove tin salts from the product the free base was generated by dissolving in H₂O (20 ml), basifying with NH₄OH and extracting with CH₂Cl₂ (7 x). The combined extracts were dried (MgSO₄) and the solvent removed under vacuum to give the desired hydrazine (5.1 g, 74%); δ (250MHz, CD₃OD) 7.20 (2H, d, J=9.0Hz, Ar—H), 7.28–7.54 (3H, m, Ar—H), 8.08 (1H, dd, J =1.5 and 8.0Hz, Ar=13 H), 8.62 (1H, dd, J=1.5 and 5.0Hz, Ar—H), 8.67 (1H, s, Ar—H).

4. N,N-Dimethyl-2-[5-(4-azabenzimidazol-1-yl)-1H-indol-3-yl) ethylamine. Oxalate. Monohydrate.

N,N-Dimethylbutanal dimethylacetal (0.36 g, 2.2 mmol) was added to a solution of the preceding hydrazine (0.5 g, 2.2 mmol) in 4% H₂SO₄ (20 ml) and the mixture refluxed for 16 h. The solution was cooled to room temperature, basified with ammonia solution and extracted with CH₂Cl₂ (3×100 ml). The combined extracts were dried (Na₂SO₄) and evaporated and the residue chromatographed on silica-gel eluting with CH₂Cl₂/MeOH/NH₃ (60:8:1) to give the desired indole (0.25 g). The oxalate monohydrate salt was prepared by adding a solution of oxalic acid in ether to a solution of the free base in MeOH/Et₂O; mp 116–118° C.; (Found: C, 58.40; H, 5.81; N, 16.89. C₁₈H₁₉N₅.C₂H₂O₄.H₂O requires C, 58.10; H, 5.61; N, 16.94%); δ (360MHz, D₂O) 2.93 (6H, s, NMe₂), 3.14 (2H, t, J=7.5Hz, CH₂), 3.44 (2H, t, J=7.5Hz, CH₂), 7.17 (1H, dd, J=1.8 and 8.6Hz, Ar—H), 7.28 (1H, dd, J=4.9 and 7.2Hz, Ar—H), 7.39 (1H, s, Ar—H), 7.51 (1H, d, J= 8.6Hz, Ar—H), 7.57 (1H, d, J=1.8Hz, Ar—H), 7.83 (1H, d, J=7.2Hz, Ar—H), 8.41 (1H, d, J=4.9Hz, Ar—H), 8.48 (1H, s, Ar—H).

EXAMPLE 2

N,N-Dimethyl-2-[5-(4,6-diazabenzimidazol-1-yl)-1H-indol-3-)ethylamine. Sesquioxalate.

1. 4-(4,6-Diazabenzimidazol-1-yl)nitrobenzene

Prepared from purine and 1-fluoro-4-nitrobenzene as described for Example 1, Step 1. The product precipitated from the reaction mixture as a single isomer; δ (D₆-DMSO) 8.16 (2H, d, J=9.0Hz, Ar—H), 8.48 (2H, d, J=9.0Hz, Ar—H), 9.13 (1H, s, Ar—H), 9.28 (1H, s, Ar= —H), 9.39 (1H, s, Ar—H).

2. 4-(4,6-Diazabenzimidazol-1-yl)phenylhydrazine, Dihydrochloride.

Prepared from the preceding nitrobenzene as described for Example 1, Steps 2 and 3; δ (360MHz, D₂O) 7.30 (2H, d, J=8.8Hz, Ar—H), 7.74 (2H, d, J=8.8Hz, Ar—H), 9.39 (1H, s, Ar—H), 9.43 (1H, s, Ar—H), 9.58 (1H, s, Ar—H).

3. 2-[5-(4,6-Diazabenzimidazol-1-yl )-1H-indol-3-yl] ethylamine

4-Chlorobutanal dimethylacetal (0.66 g, 4.3 mmol) was added to a solution of the preceding hydrazine (1.1 g, 3.9 mmol) in EtOH/H₂O (50 ml, 5:1) and the mixture refluxed for 3 h. The resultant precipitate was filtered off, taken up into 2N NaOH (10 ml) and extracted with CH₂Cl₂ (4×50 ml). The combined extracts were dried (Na₂SO₄) and evaporated to give the title-tryptamine (0.15 g); δ (360MHz, CD₃OD) 3.06–3.20 (6H, m, 2 of CH₂), 7.32 (1H, s, Ar—H), 7.34 (1H, dd, J=1.7 and 8.5Hz, Ar—H), 7.57 (1H, d, J=8.5Hz, Ar—H), 7.82 (1H, d, J=1.7Hz, Ar—H), 8.81 (1H, s, Ar—H), 8.99 (1H, s, Ar—H), 9.02 (1H, s, Ar—H).

4. N,N-Dimethyl-2-[5-(4,6-diazabenzimidazol-1-yl)-1H-indol- 3-yl]ethylamine. Sesquioxalate.

A solution of formaldehyde (0.18 g of a 38% ww solution in H₂O, 2.2 mmol) in MeOH (25 ml) was added to a stirred solution of the preceding tryptamine (0.23 g, 0.83 mmol), NaCNBH₃ (0.134 g, 2.08 mmol) and MeCO₂H (0.275 g, 4.7 mmol), in MeOH (25 ml), at room temperature. After 2 h, a saturated solution of K₂CO₃ (10 ml) was added and the solvent removed under vacuum. The aqueous residue was extracted with ethyl acetate (3×50 ml), the combined extracts dried (Na₂ SO₄) and evaporated. The crude product was chromatographed on silica-gel eluting with CH₂Cl₂/MeOH/NH₃ (50:8:1) to give the title-product. The sesquioxalate salt was prepared, mp 208°–210° C. (MeOH); (Found: C, 54.24; H, 5.08; N, 19.07. C₁₇H₁₈N₆.1.5(C₂H₂O₄) requires C, 54.42; H, 4.80; N, 19.04%); δ (360MHz, D₂O) 2.94 (6H, s, NMe₂), 3.14 (2H, t, J=7.0Hz, CH₂), 3.48 (2H, t, J=7.0Hz, CH₂), 7.25 (1H, d, J=8.3Hz, Ar—H), 7.38 (1H, s, Ar—H), 7.45 (1H, d, J=8.3Hz, Ar—H), 7.64 (1H, s, Ar—H), 8.80 (1H, s, Ar—H), 8.93 (2H, s, Ar—H).

EXAMPLE 3

N,N-Dimethyl-2-[5-(4,6-diazabenzimidazol-1-ylmethyl)-1H-indol-3-yl] ethylamine. Oxalate.

1. 4-Cyanophenylhydrazine. Hydrochloride

To a cooled (–15° C.) and stirred suspension of 4-aminobenzonitrile (50 g, 423 mmol) in concentrated hydrochloric acid (550 ml) was added dropwise a solution of sodium nitrite (31.5 g, 457 mmol) in water (200 ml) at such a rate as to maintain the temperature below –10° C. After the addition was finished, the reaction mixture was quickly filtered to remove solids and the filtrate was added portionwise to a cooled (–20° C.) and stirred solution of tin (II) chloride dihydrate (477 g, 2.1 mol) in concentrated hydrochloric acid (370 ml) at such a rate as to maintain the temperature below –10° C. After further 15 minutes at –10° to 0° C., the white precipitate was collected by filtration, washed with diethyl ether (4×250ml) and dried to give 56 g (78%) of the title compound; mp 235°–237° C. (ethanol-water 1:1); ¹H NMR (250MHz, D₆-DMSO) δ10.50 (3H, br s, –N⁺H₃) 9.10 (1H, br s, —NH—), 7.71 (2H, d, J=8.8Hz, Ar—H), 7.03 (2H, d, J=8.8Hz, Ar—H); m/z (CI) 132 (M⁺–1).

2. 2-[5-Cyano-1H-indol-3-yl]ethylamine. Hydrochloride.

To a stirred suspension of 4-cyanophenylhydrazine (50 g) in a mixture of ethanol and water (5:1; 21) was added 4-chlorobutanal dimethylacetal (45 g) and the resulting mixture was refluxed for 18 hours. Solvents were removed under vacuum and the residue was azeotroped with toluene to give a brown solid. Crystallisation of this crude material from methanol (150 ml) gave 23 g (35%) of the title compound as a yellow solid; mp 270°–274° C.; ¹H NMR (250MHz, D₆-DMSO) δ 11.60 (1H, br s, indole N—H), 8.17 (1H, d, J=1.1Hz, Ar—H), 7.97 (3H br s, –N⁺H₃), 7.54 (1H, d, J=8 5Hz, Ar—H), 7.46 (1H, s, Ar—H), 7.44 (1H, dd, J=8.5 and 1.1Hz, Ar—H), 3.05 (4H, br s, —CH₂CH₂N—); m/z (CI) 184 (M⁺–1).

3. N-tert-Butyloxycarbonyl-2-[5-cyano-1H-indol- 3-yl] ethylamine.

The title compound was prepared in 58% yield from the preceding tryptamine using (BOC)₂O and NEt₃ in CH₂Cl₂. The product was obtained as a white solid; mp 132°–134° C. (hexane-ethyl acetate); ¹H.NMR (250MHz, CDCl₃) δ 8.42 (1H, br s, indole N—H), 7.93 (1H, s, Ar—H), 7.41 (2H, s, Ar—H), 7.12 (1H, d, J=2.2Hz, Ar—H), 4.71 (1H, br s, —NH—), 3.44 (2H, q, J=6.9Hz, —CH₂NH—), 2.94 (2H, t, J= 6.9Hz, Ar—CH₂—), 1.45 (9H, s, t—Bu); m/z (CI) 286 (M⁺+1).

4. N-tert-Butyloxycarbonyl-2-[5-aminomothyl-1H-indol-3-yl]ethylamine

A solution of the product from the previous step (11.3 g) in a mixture of absolute ethanol (750 ml) and chloroform (22 ml) was hydrogenated at 50 psi over platinum (IV) oxide (1 g) for 28 hours. The catalyst was removed by filtration and solvents were removed under vacuum. Flash chromatography of the residue (silica gel, dichloromethane-methanol-ammonia 90:10:1) gave 9.5 g (82%) of the title compound as a white solid; mp 147°–149° C.; $^1$H NMR (360MHz, CDCl$_3$) δ8.04 (1H, br s, indole N—H), 7.52 (1H, s, Ar—H), 7.33 (1H, d, J =8.4Hz, Ar—H), 7.16 (1H, d, J=8.4Hz, Ar—H), 7.03 (1H, s, Ar—H), 4.61 (1H, br s, —NHBOC), 3.96 (2H, s, Ar—CH$_2$NH$_2$), 3.45 (2H, br q, —CH$_2$NHBOC), 2.95 (2H, t, J=6.8Hz, Ar—CH$_2$—), 1.43 (9H, s, t—Bu); m/z (CI)288 (M$^+$–1).

5. N-tert-Butyloxycarbonyl-2-[5-dimethylaminomethyl-1H-indol-3-yl]ethylamine

The title compound was prepared in 71% yield from the product from the previous step using the conditions described for Example 2, Step 4; colourless thick oil; $^1$H NMR (250MHz, CDCl$_3$) δ8.07 (1H, br s, indole N—H), 7.50 (1H, s, Ar—H), 7.31 (1H, d, J=8.3Hz, Ar—H), 7.16 (1H, d, J=8.3Hz, Ar—H), 7.02 (1H, s, Ar—H), 4.61 (1H, br s, —NH—), 3.54 (2H, s, Ar—CH$_2$N—), 3.45 (2H, q, J=6.2Hz, —CH$_2$NH—), 2.94 (2H, t, J=6.2Hz, Ar—CH$_2$—), 2.27 (6H, s, —NMe$_2$), 1.43 (9H, s. t—Bu).

6. N-tert-Butyloxycarbonyl-2-[5-trimethylammonium methyl-1H-indol-3-yl]ethylamine. Iodide.

A solution of the product from step 5 (2.9 g) in a mixture of anhydrous diethyl ether (170 ml) and iodomethane (36 ml) was allowed to stand at room temperature for 16 hours in the dark. The white solid was collected by filtration, washed with diethyl ether and dried over phosphorous pentoxide at 50° C. under vacuum to give 4.2 g (100%) of the title compound; mp 199°–202° C. (decomposition); $^1$H NMR (360MHz, DMSO-d$_6$) δ 11.09 (1H, br s, indole N—H), 7.69 (1H, s, Ar—H), 7.44 (1H, d, J=8.3Hz, Ar—H), 7.26 (1H, s, Ar—H), 7.19 (1H, d, J= 8.3Hz, Ar—H), 6.89 (1H, br t, —NH—), 4.57 (2H, s, Ar—CH$_2$N—), 3.23 (2H, q, J=7.6Hz, —CH$_2$NH—), 3.01 (9H, s —N$^+$Me$_3$), 2.83 (2H, t, J=7.6Hz, Ar—CH$_2$—), 1.37 (9H, s, t—Bu); m/z (FAB) 332. (Found: C, 49.30; H, 6.55; N, 8.79. C$_{19}$H$_{30}$IN$_3$O$_2$ requires: C, 49.68; H, 6.58; N, 9.15%).

7. N-(tert-Butyloxycarbonyl-2-[5-(4,6-diazabenzimidazol-1 -ylmethyl)-1H-indol-3-yl]ethylamine Sodium hydride (0.185 g, 7.7 mmol, 60% dispersion in oil) was added to a stirred solution purine (0.5 g, 4.2 mmol) in DMF (50 ml). The mixture was stirred at room temperature for 0.25 h before adding the preceding methiodide (1.0 g, 2.2 mmol) and refluxing for 16 h. The solution was cooled to room temperature before adding H$_2$O (50 ml) and extracting with EtOAc (3 x). The combined organics were washed with brine (2 x), dried (Na$_2$SO$_4$) and evaporated. The crude product was purified by chromatography on silica-gel eluting with EtOAc/MeOH/NH$_3$ (90:2:0.5_50:6:0.5) to give 2 products. The less polar isomer (0.14 g) was identified as the 5,7-diazabenzimidazole adduct; δ (360MHz, CDCl$_3$) 1.46 (9H, s, (CH$_3$)$_3$), 2.96 (2H, t, J=7.0Hz, CH$_2$), 3.38–3.52 (2H, m, CH$_2$), 5.54 (2H, s, CH$_2$), 7.08 (1H, d, J=1.5H Ar—H), 7.16 (1H, dd, J=1.5 and 8.5Hz, Ar—H), 7.34 (1H, d, J=8.5Hz, Ar—H), 7.64 (1H, s, Ar—H), 8.06 (1H, s, Ar—H), 8.46 (1H, br s, NH), 9.04 (1H, s, Ar—H), 9.14 (1H, s, Ar—H). The more polar product was identified as the title-tryptamine (0.55 g) δ (360MHz, CDCl$_3$) 1.43 (9H, s, (CH$_3$)$_3$), 2.93 (2H, t, J=6.8Hz, CH$_2$), 3.43 (2H, br s, CH$_2$), 5.52 (2H, s, CH$_2$), 7.04 (1H, d, J=8.3Hz, Ar—H), 7.12 (1H, s, Ar—H), 7.27 (1H, s, Ar—H), 7.37 (1H, d, J=8.3Hz, Ar—H), 7.61 (1H, s, N—H), 8.30 (1H, s, Ar—H), 8.49 (1H, s, N—H), 8.76 (1H, s, Ar—H), 9.10 (1H, s, Ar-H).

8. 2-[5-(4,6-Diazabenzimidazol-1-ylmethyl)-1H-indol-3-yl] ethylamine

The preceding NHBOC-tryptamine (0.45 g, 1.1 mmol) was added to 90% formic acid (50 ml), at 0° C. The mixture was warmed to room temperature and stirred for 4 h before adding methanol (50 ml) and evaporating the solvents under vacuum. The residue was chromatographed on silica-gel eluting with CH$_2$Cl$_2$/MeOH/NH$_3$ (30:8:1) to afford the title-tryptamine (69 mg); δ(360MHz, CD$_3$OD) 2.86–2.91 (4H, m, 2 of CH$_2$), 5.58 (2H, s, CH$_2$), 7.06 (1H, dd, J=1.5 and 8.4Hz, Ar—H), 7.07 (1H, s, Ar—H), 7.29 (1H, d, J=8.4Hz, Ar—H), 7.61 (1H, s, Ar—H), 8.64 (1H, s, Ar—H), 8.79 (1H, s, Ar—H), 8.84 (1H, s, Ar—H).

9. N,N-Dimethyl-2-[5-(4,6-diazabenzimidazol-1-ylmethyl)-1 H-indol-3-yl]ethylamine. Oxalate.

Prepared from the preceding tryptamine using the procedure described for Example 2, Step 4. The oxalate salt was prepared, mp 210°–212° C. ($^i$PrOH/MeOH/Et$_2$O); (Found: C, 57.36; H, 5.44; N, 19.21. C$_{18}$H$_{20}$N$_6$.1.2 (C$_2$H$_2$O$_4$) requires C, 57.19; H, 5.27; N, 19.61%); δ (360MHz, D$_2$O) 2.89 (6H, s, NMe$_2$), 3.20 (2H, t, J=7.4Hz, CH$_2$), 3.44 (2H, t, J=7.4Hz, CH$_2$), 5.65 (2H, s, CH$_2$), 7.22 (1H, d, J=8.4Hz, Ar—H), 7.35 (1H, s, Ar—H), 7.50 (1H, s, Ar—H), 7.68 (1H, s, Ar—H), 8.74 (1H, s, Ar—H), 8.88 (1H, s, Ar—H), 8.91 (1H, s, Ar—H).

EXAMPLE 4

N,N-Dimethyl-2-[5-(5,7-diazabenzimidazol-1-ylmethyl)-1H-indol-3-yl] ethylamine. Sesquioxalate. Hemihydrate.

1. 2-[5-(5,7-Diazabenzimidazol-1-ylmethyl)-1H-indol-3-yl] ethylamine

Prepared from N-tert-butyloxycarbonyl-2-[5-(5,7-diazabenzimidazol-1 -ylmethyl)-1H-indol-3-yl]ethylamine using the procedure described for Example 3, Step 8; δ (250MHz, CDCl$_3$) 2.88 (2H, t, J=7.4Hz, CH$_2$), 3.02 (2H, t, J=7.4Hz, CH$_2$), 5.56 (2H, s, CH$_2$), 7.08 (1H, d, J=1.5Hz, Ar—H), 7.18 (1H, dd, J=1.5 and 8.4Hz, Ar—H), 7.34 (1H, d, J=8.4Hz, Ar—H), 7.64 (1H, s, Ar—H), 8.06 (1H, s, Ar—H), 8.44 (1H, br s, NH), 9.04 (1H, s, Ar—H), 9.16 (1H, s, Ar—H).

2. N,N-Dimethyl-2-[5,7-diazabenzimidazol-1-ylmethyl)-1H-indol-3-yl]ethylamine. Sesquioxalate. Hemihydrate.

Prepared from the preceding tryptamine using the procedure described for Example 2, Step 4. The sesquioxalate hemihydrate salt was prepared, mp 105°–107° C. ($^i$PrOH/MeOH/NH$_3$); (Found: C, 54.02; H, 5.62; N, 17.99. C$_{18}$H$_{20}$N$_6$.1.5(C$_2$H$_2$O$_4$).0.7 H$_2$O requires C, 53.89; H, 5.25; N, 17.96%); δ (360MHz, D$_2$O) 2.89 (6H, s, NMe$_2$), 3.19 (2H, t, J= 7.4Hz, CH$_2$), 3.45 (2H, t, J=7.4Hz, CH$_2$), 5.60 (2H, s, CH$_2$), 7.22 (1H, dd, J=1.5 and 8.4Hz, Ar—H), 7.33 (1H, s, Ar—H), 7.48 (1H, d, J=8.4Hz, Ar—H), 7.66 (1H, s, Ar—H), 8.58 (1H, s, Ar—H), 8.94 (1H, s, Ar—H), 9.12 (1H, s, Ar—H).

EXAMPLE 5

Tablet Preparation

Tablets containing 1.0, 2.0, 25.0, 26.0, 50.0 and 100.0 mg, respectively of the following compounds are prepared as illustrated below:

N,N-Dimethyl-2-[5-(4-azabenzimidazol-1-yl)-1H-indol-3-yl) ehylamine. Oxalate. Monohydrate.

N,N-Dimethyl-2-[5-(4,6-diazabenzimidazol-1-yl)-1H-indol-3-yl)ethylamine. Sesquioxalate.

N,N-Dimethyl-2-[5-(4,6-diazabenzimidazol-1-ylmethyl)-1H-indol-3-yl] ethylamine. Oxalate.

N,N-Dimethyl-2-[5-(5,7-diazabenzimidazol-1-ylmethyl)-1H-indol-3-yl] ethylamine. Sesquioxalate. Hemihydrate.

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

I claim:

1. A compound of formula I, or a pharmaceutically acceptable salt or prodrug thereof:

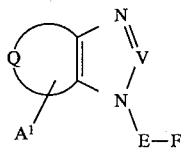
(I)

wherein

Q represents the residue of a six-membered aromatic or heteroaromatic nucleus containing zero, one or two nitrogen atoms;

$A^1$ represents hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$;

V represents nitrogen or C—$A^2$;

E represents a bond or a straight or branched alkylene chain containing from 1 to 4 carbon atoms;

F represents a group of formula

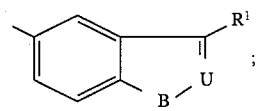
;

U represents nitrogen or C—$R^2$;

B represents oxygen, sulphur or N—$R^3$;

$R^1$ represents —$CH_2$—$CHR^4$—$NR^6R^7$ or a group of formula (i), (ii), (iii) or (iv):

(i)

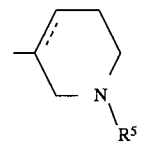
(ii)

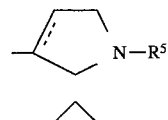
(iii)

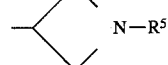
(iv)

in which the broken line represents an optional chemical bond;

$A^2$, $R^2$, $R^3$, $R^4$, $R^5$, $R^6$ and $R^7$ independently represent hydrogen or $C_{1-6}$ alkyl;

$R^x$ and $R^y$ independently represent hydrogen, hydrocarbon or a heterocyclic group, or $R^x$ and $R^y$ together represent a $C_{2-6}$ alkylene group;

$R^z$ represents hydrogen, hydrocarbon or a heterocyclic group;

T represents oxygen, sulphur or a group of formula =N.G; and

G represents hydrocarbon, a heterocyclic group or an electron-withdrawing group.

2. A compound as claimed in claim 1 represented by structure IA:

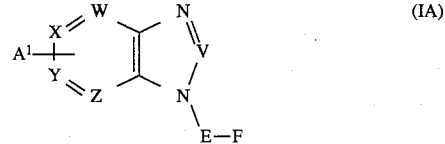
(IA)

in which zero, one or two of W, X, Y and Z represent nitrogen and the remainder represent carbon; and $A^1$, V, E and F are as defined in claim 1.

3. A compound as claimed in claim 2 wherein W represents nitrogen, X and Z each represents carbon and Y represents nitrogen or carbon.

4. A compound as claimed in claim 2 wherein Z represents nitrogen, W and Y each represents carbon and X represents nitrogen or carbon.

5. A compound as claimed in claim 1 represented by formula IIA, and pharmaceutically acceptable salts and prodrugs thereof:

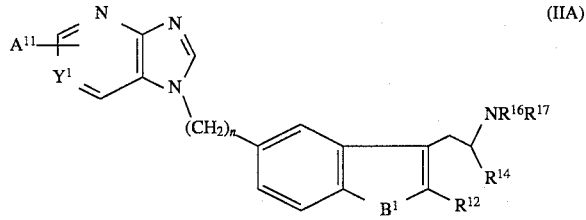
(IIA)

wherein $Y^1$ represents nitrogen or carbon;

n is zero, 1, 2 or 3;

$B^1$ represents oxygen, sulphur or $N-R^{13}$;

$A^{11}$ represents $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$) alkylamino, any of which groups may be optionally substituted; or hydrogen, halogen, cyano, trifluoromethyl or amino; and $R^{12}$, $R^{13}$, $R^{14}$, $R^{16}$ and $R^{17}$ independently represent hydrogen or $C_{1-6}$ alkyl.

6. A compound as claimed in claim 1 represented by formula IIB, and pharmaceutically acceptable salts and prodrugs thereof:

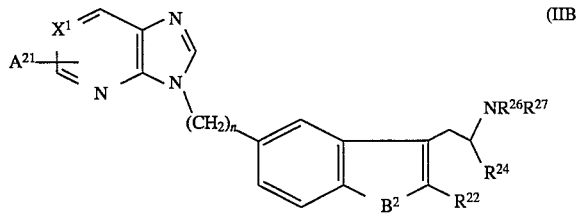

(IIB)

wherein $X^1$ represents nitrogen or carbon;

n is zero, 1, 2 or 3;

$B^2$ represents oxygen, sulphur or $N-R^{23}$;

$A^{21}$ represents $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino; and $R^{22}$, $R^{23}$, $R^{24}$, $R^{26}$ and $R^{27}$ independently represent hydrogen or $C_{1-6}$ alkyl.

7. A compound as claimed in claim 1 selected from:

N,N-dimethyl-2-[5-(4-azabenzimidazol-1-yl) -1H-indol-3yl]ethylamine;

N,N-dimethyl-2-[5-(4,6-diazabenzimidazol-1-yl) -1H-indol-yl]ethylamine;

N,N-dimethyl-2-[5-(4,6-diazabenzimidazol-1-ylmethyl) -1H-indol-3-yl]ethylamine; N,N-dimethyl-2-[5-(5,7-diazabenzimidazol-1-ylmethyl)-1H -indol-3-yl]ethylamine;

and salts and prodrugs thereof.

8. A pharmaceutical composition comprising a compound as claimed in claim 1 in association with a pharmaceutically acceptable carrier or excipient.

9. A method for the treatment and/or prevention of clinical conditions for which a selective agonist of 5-HT$_1$-like receptors is indicated, which method comprises administering to a patient in need of such treatment an effective amount of a compound of formula I as defined in claim 1, or a pharmaceutically acceptable salt thereof or a prodrug thereof.

* * * * *